(12) United States Patent
Senegas

(10) Patent No.: US 10,595,910 B2
(45) Date of Patent: Mar. 24, 2020

(54) DYNAMICALLY STABILIZING VERTEBRAL IMPLANT, AND SURGICAL KIT COMPRISING SAME

(71) Applicant: BACKBONE, Le Bouscat (FR)

(72) Inventor: Jacques Senegas, Mérignac (FR)

(73) Assignee: BACKBONE, Le Bouscat (FR)

( * ) Notice: Subject to any disclaimer, the term of this patent is extended or adjusted under 35 U.S.C. 154(b) by 0 days.

(21) Appl. No.: 16/086,504

(22) PCT Filed: Feb. 15, 2017

(86) PCT No.: PCT/FR2017/050346
§ 371 (c)(1),
(2) Date: Sep. 19, 2018

(87) PCT Pub. No.: WO2017/140984
PCT Pub. Date: Aug. 24, 2017

(65) Prior Publication Data
US 2019/0099206 A1    Apr. 4, 2019

(30) Foreign Application Priority Data
Feb. 15, 2016   (FR) ..................................... 16 51203

(51) Int. Cl.
*A61B 17/70*   (2006.01)
*A61F 2/44*   (2006.01)
(Continued)

(52) U.S. Cl.
CPC ...... *A61B 17/7062* (2013.01); *A61B 17/7053* (2013.01); *A61B 17/7064* (2013.01);
(Continued)

(58) Field of Classification Search
CPC . A61B 17/70; A61B 17/7053; A61B 17/7062; A61B 17/7064; A61B 17/7067;
(Continued)

(56) References Cited

U.S. PATENT DOCUMENTS

| 8,403,964 B2 * | 3/2013 | Fielding ............. | A61B 17/7062 606/246 |
| 8,663,283 B2 * | 3/2014 | Belliard ............. | A61B 17/7053 606/248 |

FOREIGN PATENT DOCUMENTS

| EP | 2 138 122 A1 | 12/2009 |
| EP | 2 351 534 A1 | 8/2011 |

(Continued)

OTHER PUBLICATIONS

International Search Report, dated Apr. 5, 2017, from corresponding PCT/FR2017/050346 application.

*Primary Examiner* — Larry E Waggle, Jr.
(74) *Attorney, Agent, or Firm* — Young & Thompson

(57) ABSTRACT

Disclosed is a dynamically stabilizing intervertebral implant composed of a stabilizing wedge (1), a blocking pin (2), a locking screw (3), and a flexible link in the form of a strap. The stabilizing wedge includes a recess (12) through which the strap can pass. The blocking pin can come into engagement with the wedge by movement inside the recess in the direction of the main axis of the body of the wedge in such a way that the longitudinal axis of the blocking pin firstly coincides with the longitudinal axis of the recess, secondly is perpendicular to the longitudinal axis of the first strap portion inside the recess, and thirdly is parallel to the surface of the first strap portion inside the recess. The strap is immobilized with respect to the stabilizing wedge by being clamped between the blocking pin and the inner wall of the recess.

20 Claims, 3 Drawing Sheets

(51) Int. Cl.
*A61F 2/46* (2006.01)
*A61B 17/82* (2006.01)
*A61B 17/84* (2006.01)

(52) U.S. Cl.
CPC ............ *A61B 17/82* (2013.01); *A61B 17/842* (2013.01); *A61F 2/44* (2013.01); *A61F 2/4405* (2013.01); *A61F 2/4611* (2013.01)

(58) Field of Classification Search
CPC ......... A61B 17/82; A61B 17/842; A61F 2/44; A61F 2/4405; A61F 2/4611
See application file for complete search history.

(56) References Cited

FOREIGN PATENT DOCUMENTS

| | | |
|---|---|---|
| EP | 2 192 863 B1 | 9/2011 |
| EP | 2 303 163 B1 | 11/2011 |
| WO | 2009/040380 A1 | 4/2009 |
| WO | 2009/141393 A1 | 11/2009 |

\* cited by examiner

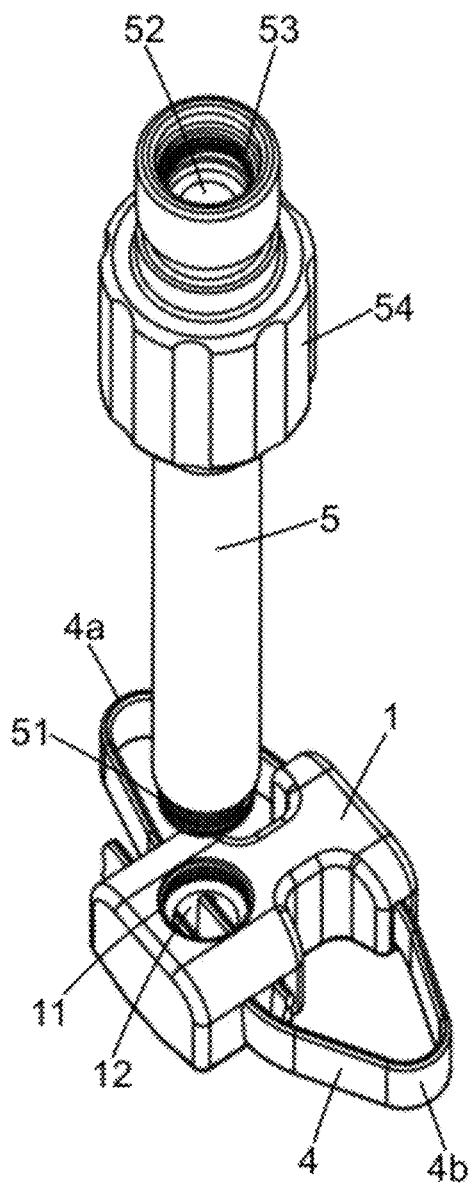
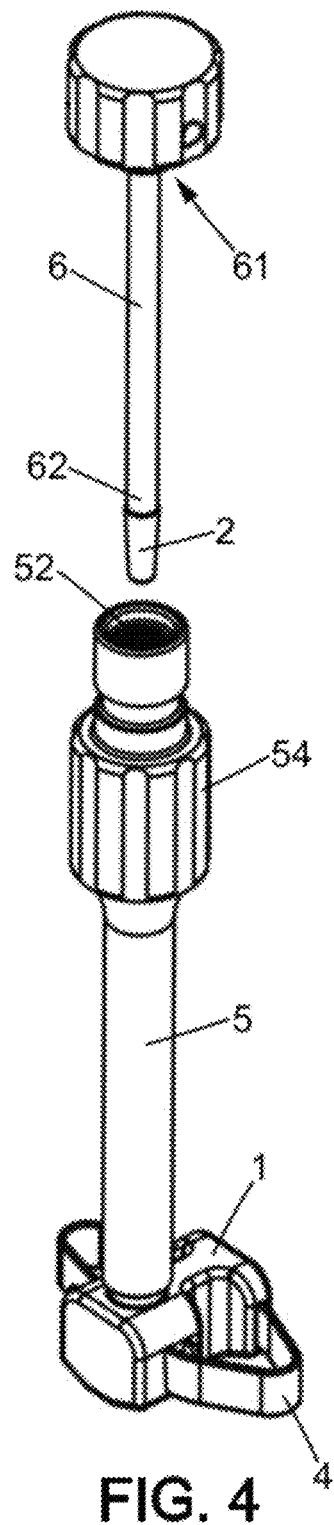
FIG. 3
FIG. 4

DYNAMICALLY STABILIZING VERTEBRAL IMPLANT, AND SURGICAL KIT COMPRISING SAME

TECHNICAL FIELD

The present invention relates generally to implants used in surgery of the spine, more particularly to a dynamically stabilizing intervertebral implant and to a surgical kit comprising same.

TECHNOLOGICAL BACKGROUND

Operations performed in surgery of the spine may concern the cervical region (neck), the thoracic region or, more frequently, the lumbar region.

When there is an instability, for example sliding of one vertebra relative to the adjacent vertebrae, an operation for stabilizing the spinal column may entail implanting metal material in the form of screws connected to each other by bars or plates. These implants form scaffolding that acts as a stabilizer for the spinal column.

In more recent techniques, the stabilization of the column can be obtained by means of an intervertebral implant composed of a stabilizing wedge, a flexible link in the form of a textile braid, a movable assembly and a locking member. The stabilizing wedge is intended to be positioned between the spinous processes of two consecutive vertebrae, that is to say adjacent vertebrae, that are to be stabilized. The flexible link (for example a textile braid) encloses the spinous processes. The movable assembly is adapted to come into engagement with the stabilizing wedge in such a way as to immobilize the flexible link with respect to the stabilizing wedge. This blocking is achieved by clamping the flexible link between the movable assembly and the stabilizing wedge. The locking member (for example a screw) is adapted to lock the engagement of the movable assembly with the stabilizing wedge, and thus the final blocking of the flexible link, which results directly from this.

PRIOR ART

An intervertebral implant of the aforementioned type is disclosed, for example, in the document EP 2192863, published by WIPO under number WO 2009/040380, and in the document EP 2303163, published by WIPO under number WO 2009/141393.

Most of the lumbar operations are performed by open surgery using a posterior approach, by making an incision in the patient's back at the level of the vertebrae that are to be stabilized.

The design of the implants of the prior art involves the surgeon having to clear quite a wide intervention region around the vertebrae that are to be stabilized, in particular for placing the one or more flexible links in the wedge, and for tensioning and blocking said one or more links.

The document EP 2138122 describes a system for stabilization between the sacrum and a lumbar vertebra. The system comprises at least one textile braid which is anchored on the sacrum by screws. To ensure that the braids are blocked with tensioning, a blocking system comprises wedging pins between the inner walls of an orifice provided in the body of the blocking system. The direction of movement of such a movable pin is tangential to the surface of the braid and is parallel to the longitudinal axis of said braid. These arrangements are not adapted to an intervertebral implant of the kind forming the subject matter of the present invention.

SUMMARY OF THE INVENTION

It is important to provide the surgeon with a dynamically stabilizing intervertebral implant which makes it possible to reduce the size of the incision to an absolute minimum in order to protect the surrounding tissue (in particular the muscle tissue that contributes to the stability of the spinal column) from the stress associated with the retraction of the surgical wound, which can cause severe necrosis. The patient's recovery after surgery is all the more rapid and the result all the more satisfactory.

To this end, a first aspect of the invention proposes a dynamically stabilizing intervertebral implant comprising:
  a stabilizing wedge adapted to stabilize at least two adjacent vertebrae by interposition between spinous processes of the vertebrae, having a substantially parallelepipedal body which has a defined main axis,
  at least one strap forming a flexible link for fixing the stabilizing wedge to the spinous processes of the vertebrae to be stabilized, said strap having first and second strap portions which each comprise one of the opposite ends of said strap, and said strap having a defined longitudinal direction and a defined strap surface,
  at least one movable assembly adapted to come into engagement with the stabilizing wedge in such a way as to immobilize the strap with respect to the stabilizing wedge by clamping of the strap between the movable assembly and the stabilizing wedge, and
  a locking member for axially locking the engagement of the movable assembly with the stabilizing wedge and thus the blocking of the strap.

According to embodiments, the body of the stabilizing wedge comprises at least one recess through which at least the first strap portion can pass, the recess having a longitudinal axis parallel to the main axis of the stabilizing wedge, and an inner wall extending parallel to said longitudinal axis of the recess with a defined shape;
  the movable assembly comprises at least one blocking pin having a defined longitudinal axis and a defined shape substantially complementing the shape of the recess, in order to come into engagement with the stabilizing wedge by movement in said recess in the direction of the main axis of the body of said wedge in such a way that the longitudinal axis of the blocking pin:
  firstly coincides with the longitudinal axis of the recess;
  secondly is perpendicular to the longitudinal axis of the first strap portion inside the recess; and
  thirdly is parallel to the surface of the first strap portion inside the recess,
  and moreover in such a way that the strap portion inside the recess is immobilized with respect to the stabilizing wedge by clamping of said strap portion forming a flexible link between the blocking pin and the inner wall of the recess.

The abovementioned main axis coincides with the axis of the posterior approach for the surgical operation to put the implant in place. Since the recess provided in the stabilizing wedge is open posteriorly when the wedge is in the installation position, its longitudinal axis corresponds to the axis of the posterior approach (in contrast, for example, to a lateral access, these terms "posterior" or "lateral" being from the vocabulary used in this field of spinal surgery). The blocking pin can thus be conveniently and usefully inserted by force into the recess along the axis of the posterior approach. The region of intervention and insertion (open surgery) can thus be reduced to the absolute minimum. The invention thus permits a truly minimally invasive procedure and short surgical treatment of the outpatient type.

In a directly complementary embodiment, provision can moreover be made that:

each of the first and second strap portions can pass through the recess provided in the stabilizing wedge, in order for the strap to form at least one loop in a plane perpendicular to the main axis of the wedge, with a cord adapted to come into engagement with one of the spinous processes of two vertebrae to be stabilized, and in which furthermore the blocking pin can come into engagement with the stabilizing wedge in the direction of the main axis of the body of said wedge, between each of the first and second strap portions (41a, 42a) inside the recess, in such a way that the longitudinal axis of the pin:

firstly coincides with the longitudinal axis of the recess;
secondly is perpendicular to the longitudinal axis of each of the two portions of the strap inside the recess; and
thirdly is parallel to the surface of each of first and second strap portions inside the recess, and moreover in such a way that each of the first and second strap portions is immobilized with respect to the stabilizing wedge by said strap portion being clamped between the pin and the respective portions of the inner wall of the recess that face each other.

In a directly complementary embodiment, the first and second strap portions can pass in opposite directions through the recess provided in the stabilizing wedge, so as to intersect in said recess, and in order for the strap to form a loop in a plane perpendicular to the main axis of the wedge, with two cords which are located respectively on either side of the stabilizing wedge in said plane and are adapted to come into engagement each with a respective one of the spinous processes of two adjacent vertebrae to be stabilized.

In one embodiment, the recess provided in the stabilizing wedge has a conical shape, and the blocking pin has a conical shape complementing the shape of the recess.

In one embodiment, the body of the stabilizing wedge comprises passages for the strap, which extend perpendicularly with respect to the main axis of the body of said wedge, of which at least one passage passes through the recess, and through which passages at least the strap can slide when it is not immobilized with respect to the stabilizing wedge.

In one embodiment, the strap is a braid made of non-resorbable textile material for medical use.

In one embodiment, the recess has an internally threaded inlet zone with a diameter larger than the diameter of the recess to the rear of said inlet zone, and in which the locking member is a screw of the same diameter as the diameter of the inlet zone of the recess, with a thread adapted to cooperate with the internal thread of the inlet zone, and with a bearing zone adapted to bear against a contact zone of the blocking pin in the recess when the screw is screwed into the internally threaded inlet zone of the recess.

In a second aspect, the invention also relates to a surgical kit comprising an implant according to the above first aspect, and a tool which assists in positioning the wedge of the implant and which is also referred to as implant holder hereinbelow, and also an insertion rod for the blocking pin of the implant.

More particularly, the kit is such that:

the implant holder has a tubular body having an an internal channel with an internal diameter slightly larger than the largest diameter of the blocking pin of the implant, and adapted to be fixed to the body of the stabilizing wedge in such a way that the channel is in parallax with the axis of the recess in the body, and the insertion rod for the blocking pin, adapted to slide in the internal channel for placing the blocking pin in the recess of the body of the stabilizing wedge.

In one embodiment, the tubular body of the implant holder can be provided, at a first end, with a thread for cooperating with the internal thread of the recess provided in the body of the stabilizing wedge. This allows the implant holder to be fixed to the implant by using the internal thread provided also for the locking screw of the implant, which locking screw is only put in place subsequently during the implantation operation.

In another embodiment, the implant holder can be provided, at a second end, with an internal thread at the inlet of the channel, and the insertion rod can be provided with a thread in order to cooperate with said internal thread in such a way that the insertion and then the screwing of the insertion rod into the channel of the implant holder drives the conical pin inside the said provided in the body of the wedge.

BRIEF DESCRIPTION OF THE DRAWINGS

Other features and advantages of the invention will become clear on reading the following description. The latter is given purely as an illustration and must be read with reference to the attached drawings, in which:

FIG. 3 is an exploded three-dimensional view of a part of the intervertebral implant and of an associated implant holder, according to embodiments;

FIG. 4 is an exploded three-dimensional view of a part of the intervertebral implant with the implant holder holder mounted on the implant, and of an insertion rod for the blocking pin according to embodiments;

DETAILED DESCRIPTION OF EMBODIMENTS

The intervertebral implant is designed to be placed between the spinous processes of two adjacent vertebrae, that is to say consecutive vertebrae in the stack of lumbar, thoracic and cervical vertebrae.

The main elements of the dynamically stabilizing intervertebral implant according to embodiments of the present invention will be described first with reference to FIGS. 1 and 2. As is shown in these figures, the implant is composed of a stabilizing wedge 1, a blocking pin 2, a locking screw 3, and a flexible link 4.

Figure 1:
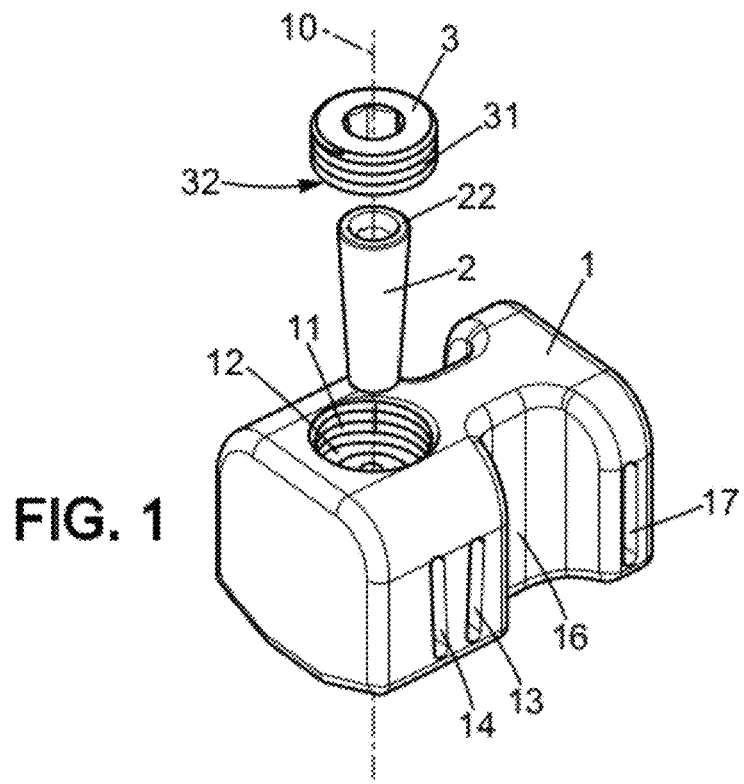
FIG. 1 is an exploded three-dimensional view of a part of the intervertebral implant according to embodiments.

The stabilizing wedge 1 comprises a generally parallelepipedal body with a main axis which, for the sake of clarity in FIG. 1, is coincident in this figure with the longitudinal axis 10 of a recess 12 which is provided in the body and which will be discussed later. FIG. 2 is a view of the implant along the longitudinal axis 10, when the implant is placed flat against the vertebrae of the patient (who is lying face down on the operating table). The main axis 10 then coincides with the axis of the posterior approach, that is to say it is perpendicular to the patient's back and therefore to the axis of the vertebral column corresponding to the direction of stacking of the vertebrae from the lumbar vertebrae to the cervical vertebrae.

As regards the descriptive terminology, the direction in which the surgeon views the implantation site is considered hereinbelow to be along the axis of the posterior approach, during the implantation procedure and when the patient is lying face down on the operating table. FIG. 2 thus shows a front view along this axis, and a plan view along this direction. The terms "posteriorly", "front" and "rear", "in front of" and "behind", "front" and "rear", "above" and "below", "upper" and "lower", and "down", "lateral" and "side", "right" and "left", especially, are used hereinbelow with reference to this convention. These terms thus correspond to the vocabulary used by persons skilled in the art of surgery of the spine.

Figure 2:
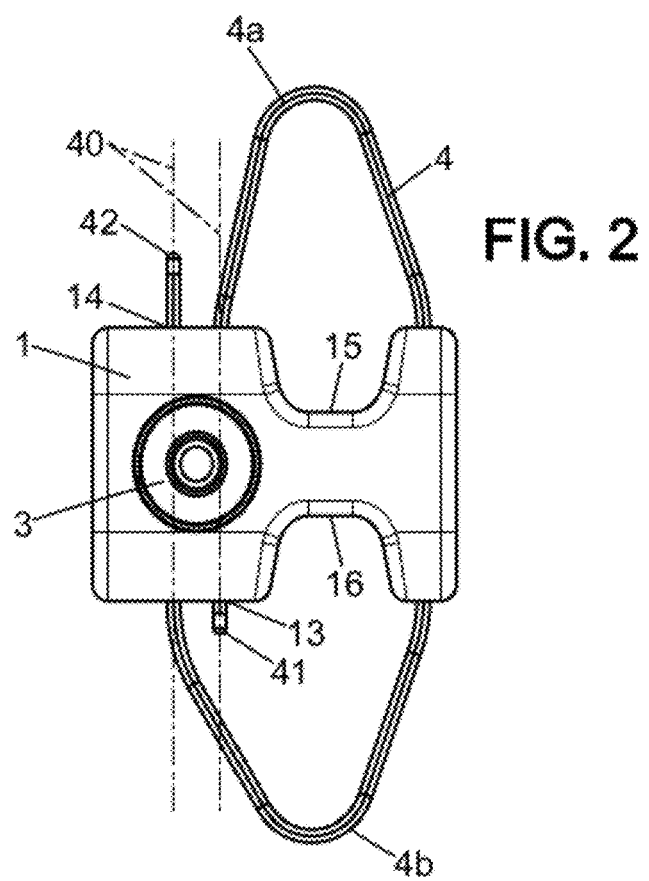
FIG. 2 is a front view, along the axis of the posterior approach, of the assembled implant according to embodiments.

The body of the stabilizing wedge 1 comprises, on a lateral face of the parallelepiped, in particular to the right in FIGS. 1 and 2, an upper indentation or notch 15 and a lower indentation or notch 16. These indentations are adapted to bear against two vertebrae to be stabilized, more particularly on the spinous process of the upper vertebra via the notch 15 and on the spinous process of the lower vertebra via the notch 16, respectively. In other words, in the installed position of the implant for stabilization of two adjacent vertebrae, the spinous processes of these vertebrae are housed in the indentations 15 and 16 of the body of the wedge 1.

As can be seen in FIG. 1, the parallelepiped of the body of the wedge 1 has softened (i.e. rounded) angles, at least on the rear face intended to be covered by flesh and skin of the patient's back. This limits the risk of inflammation or damage to the dorsal flesh in contact with the implant. This likewise reduces the discomfort or indeed the pain that the patient may feel if pressure is applied to this region of his back, for example when resting against a support (for example a seat back) or lying on his back (for example on a hard surface such as the ground).

The blocking pin 2 can have a cylindrical and conical shape, that is to say the shape of a cylinder whose cross-sectional diameter (circular) gradually decreases along its longitudinal axis. In FIG. 1, again for the sake of clarity of the drawing, the longitudinal axis of the pin coincides with the main axis 10 of the body 1 of the wedge and with the longitudinal axis of the recess 12.

The pin 2 is adapted to cooperate with the recess 12 provided in the body of the wedge 1, for example on the lateral face of the parallelepiped opposite to the face where the indentations 15 and 16 are located (i.e. to the left in FIGS. 1 and 2). For this purpose, the pin 2 and the recess 12 have shapes that complement each other. In the example shown, the pin has the shape of a conical cylinder, and the recess likewise has the shape of hollow conical cylinder with an aperture angle equal to that of the pin and an aperture diameter slightly greater than said diameter of the pin.

The recess opens out at least on the rear face of the wedge 1, and preferably on each of the front and rear faces of the wedge, as is shown in FIGS. 5A-5B, 6A-6B and 7A-7B. The diameter of the opening is substantially larger than the largest diameter of the pin and is constant in an inlet zone of the recess on the rear face via which the pin 2 is intended to enter with its tapered end. In this inlet zone of the recess, its walls have an internal thread 11 for the locking screw, which will be discussed later. The length of the inlet zone, along the longitudinal axis, is at least equal to the thickness of the locking screw 3. In front of this inlet zone, the shape of the recess is conical, without an internal thread (smooth walls), and substantially corresponds to the complementary shape of the pin, that is to say the shape is conical with the same aperture angle as that of the pin but with a slightly larger diameter in order to receive the pin and the braid, as will be explained later. In other words, in front of the internally threaded inlet zone of the recess, the diameter of the recess progressively decreases along its longitudinal axis 10 toward the front. In particular, the length of the conical part of the recess along the longitudinal axis of the recess is substantially equal to the length of the blocking pin 2 in its longitudinal direction.

The locking screw 3 is also shown in FIG. 1 in parallax with the main axis 10 of the body 1 of the wedge and the longitudinal axis of the recess 12. The screw 3 has a diameter larger than the largest diameter of the pin. This diameter corresponds to that of the internally threaded inlet zone of the recess 12. The screw 3 has an external thread 31, adapted to cooperate with the internal thread 11 of the recess 12.

The screw 3 additionally has a bearing zone 32, facing downward in FIG. 1, capable of abutting against a contact zone 22 at the rear of the pin 2. In one embodiment, the bearing zone 32 of the screw 3 and/or the contact zone 22 of the pin 2 are circular planar surfaces.

The function of the screw 3 is to lock the position of the pin 2 engaged in the recess 12. Another function of the screw, according to some embodiments, is to adjust the axial position of the pin in the recess: by turning the screw 3 engaged in the recess 12 via their respective threads, the screw rests with its surface 32 against a contact surface 22 on the rear of the pin 2, such that the latter advances through the recess 12 along its longitudinal axis, from the rear face of the wedge to the front face thereof. Details of this positional adjustment will be given later with reference to FIGS. 5A-5B, 6A-6B and 7A-7B.

The flexible link 4 can be a braid made of a textile material for medical use (non-resorbable), for example polyethylene terephthalate (PET) or polyethylene (PE). These materials can be chosen by reason of their biocompatibility and their high degree of chemical inertness. In the installed position of the implant, the flexible link 4 encloses the spinous processes in a similar way to that described in EP 2192863, particularly as shown in FIGS. 3, 10 and 11A of said published document.

The flexible link 4 preferably has the form of a strap (i.e. a tape), with a longitudinal axis and a strap surface extending along said longitudinal direction. It can pass through a passage 17 of the body of the wedge, provided in the caudal end of the body of the wedge on the right-hand side thereof, that is to say the side of the indentations 15 and 16 that is opposite to the recess 12. The passage 17 extends through the body of the wedge 1 perpendicularly with respect to the main axis 10 of the body 1 of the wedge. When not immobilized with respect to the wedge, the flexible link 4 can slide in the passage 17.

The flexible link 4 can also pass through the recess 12. For this purpose, the body of the wedge can have two other passages 13 and 14 extending right through the body 1 perpendicularly with respect to the main axis 10 of the body 1 of the wedge. The passages 13 and 14 thus extend perpendicularly with respect to the main axis 10 of the body 1 of the wedge. At least one of the passages 13 and 14, preferably both passages 13 and 14, pass(es) through the recess 12. In other words, the passages 13 and 14 open into the recess, in each case by the front end and the rear end. In the embodiment shown, the two passages 13 and 14 thus extend through the recess 12, but this is not obligatory, and it would be possible for just one of the passages 13 and 14 to extend through the recess 12. When it is not immobilized with respect to the wedge 1, the flexible link 4 can slide in the passages 13 and 14.

The flexible link 4 is inserted manually by the surgeon, for example first through the passage 17. Then the two ends 41 and 42 of the flexible link 4 are in turn inserted into the passages 13 and 14 after having engaged them above and below the spinous processes of the upper and lower vertebrae, respectively.

More particularly, the strap then forms a loop in a plane perpendicular to the main axis 10 of the wedge 1, with at least one and preferably two cords 4a and 4b respectively located on either side of the wedge in said plane. These cords 4a and 4b of the textile braid are each adapted to come into engagement respectively with one of the spinous processes of the two vertebrae to be stabilized.

The blocking pin 2 can be engaged with the stabilizing wedge in the direction of the main axis 10 of the body 1 of the wedge between each of the strap portions inside the recess, such that the longitudinal axis of the pin:

firstly coincides with the longitudinal axis 10 of the recess;

secondly is perpendicular to the longitudinal axis 40 of each of the two portions of the strap inside the recess; and, thirdly is parallel to the surface of each of the two strap portions inside the recess (i.e. the strap portions at the ends 41 and 42, respectively, of the strap).

In addition, each of the portions of the strap, at its ends 41 and 42 respectively, is then immobilized with respect to the wedge 1. This blocking is obtained by clamping said strap portions between the pin and the respective portions of the inner wall of the recess 12 that face each other.

Figure 5A:
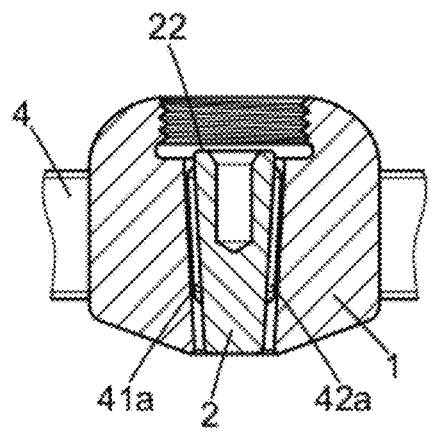
FIG. 5A and FIG. 5B are a sectional view and a three-dimensional sectional view, respectively, of the stabilizing wedge provided with the strap and the installed blocking pin, according to embodiments.
Figure 6A:
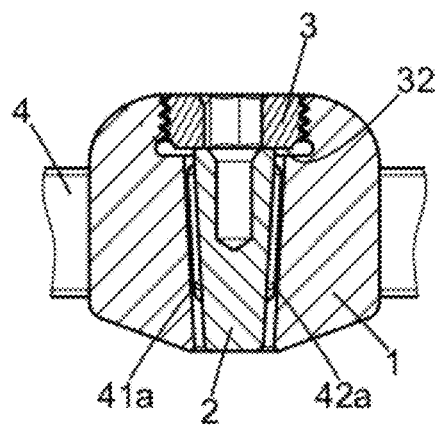
FIG. 6A and FIG. 6B are views identical to those of FIGS. 5A and 5B, respectively, additionally showing the locking screw engaged at the inlet of the recess in the wedge.
Figure 7A:
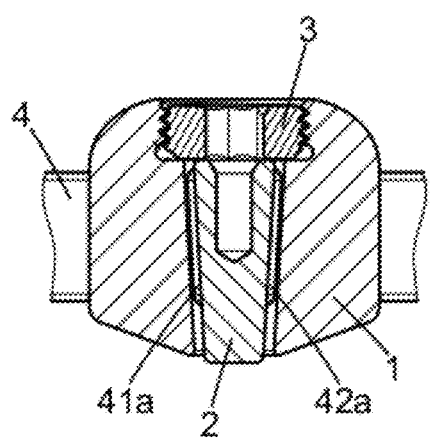
FIG. 7A and FIG. 7B are views identical to those of FIGS. 5A and 5B, respectively, additionally showing the locking screw in the locking position.
Figure 7B:
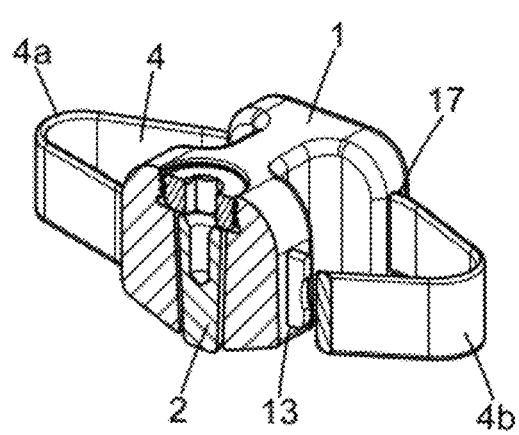

To illustrate this blocking of the two portions of the strap 4 by the pin 2, the central part of FIGS. 5A, 6A and 7A, corresponding to the internal space of the recess (which receives the pin 2), is shown along a section plane at 90 degrees to the section plane of the body 1 of the wedge in the same figures. Thus, FIGS. 5A, 6A and 7A show, at their center, a sectional view of the portions 41a and 42a of the strap 40 at the ends 41 and 42, respectively, of said strap.

In one embodiment, these two end portions 41a and 42a of the strap can pass in opposite directions through the recess 12 provided in the wedge 1, so as to intersect in said recess and form the cords 4a and 4b. This embodiment is shown in the figures. However, it is not exclusive. Indeed, the two end portions 41a and 41b of the strap could extend parallel to each other through the passages 13 and 14, and therefore through the recess 12, given another form of engagement with the spinous processes of the vertebrae to be stabilized, and also given another shape of the stabilizing wedge. In particular, in such an embodiment, the strap would form only one cord, so that two straps would be used, namely one for each of the vertebrae, with the same wedge.

To facilitate the procedure of insertion through the passages 13 and 14, the ends 41 and 42 of the strap can be reinforced, for example by treatment with ultrasonic welding, by addition of material, or by an endpiece made of titanium, or of any other suitable material, or by any other equivalent means.

Advantageously, the means for blocking and locking the flexible link 4, which comprise the pin 2 and the screw 3, are put in place via the rear face of the stabilizing wedge 1. This arrangement allows the surgeon to reduce the size of the incision to an absolute minimum, thereby preserving the integrity of the surrounding organic tissue, especially the muscles of the back.

Figure 5B:
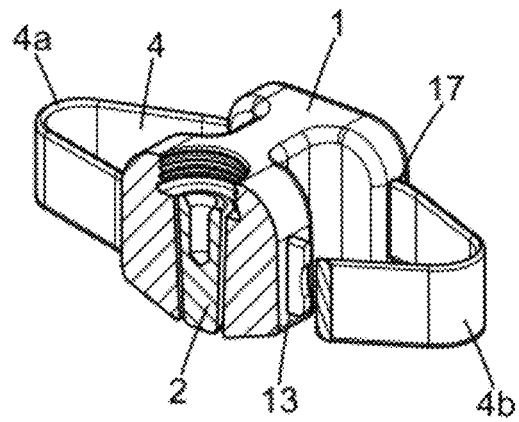
Figure 6B:
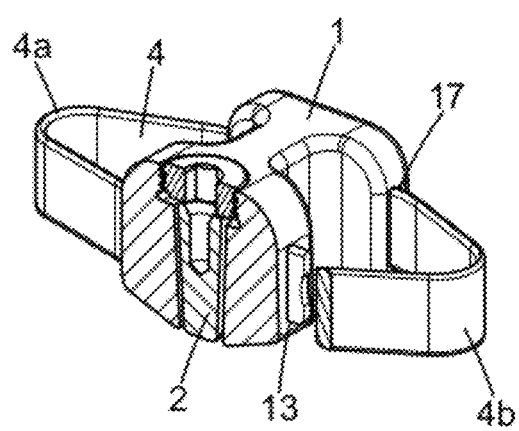

After the flexible link 4 has been put in place and tensioned with the aid of a suitable tool (procedure not described in the context of the present description), the blocking pin 2 is inserted into the recess 12, between the two end portions of the flexible link 4. The insertion of the pin 2 causes the clamping of the portions of the flexible link 4, between the outer circumferential surface of the pin 2 and the opposite inner wall of the recess 12, and stabilizes the flexible link 4. By virtue of this compression of the flexible link 4, the latter can no longer slide in the passages 13, 14 and 17. The locking screw 3 is then engaged in the recess 12, for example by hand (with or without the aid of a tool holder), once the pin 2 has been inserted fully into the internally threaded portion 11 of the recess 12, as shown in FIGS. 5A and 5B. This procedure is illustrated in FIGS. 6A and 6B. The function of the screw 3 is to secure (axially) the engagement of the blocking pin 2 in the recess 12.

The method by which the blocking pin 2 is put in place makes use of an implant holder 5 and an insertion rod 6, which are shown in FIGS. 3 and 4. The implant holder 5 is, for example, a hollow tube, that is to say it has a tubular body having an internal channel 52. The channel 52 is, for example, of constant circular cross section, with an internal diameter slightly larger than the largest diameter of the blocking pin 2.

At one of the ends of the tube 5, an internal thread 53 can be provided at the entry to the channel 52. Likewise, gripping means 54, which may be in the form of a fluted collar surrounding the tube 5 as shown, can be provided at this inlet end of the tube 5.

At the other of its ends, the tube 5 is provided with an external thread 51 which cooperates with the internal thread 11 of the stabilizing wedge 1. The implant holder 5 can thus be screwed into the stabilizing wedge 1, with the internal channel 52 aligned with the longitudinal axis 10 of the recess 2, that is to say in parallax with the recess 12, for the purpose of inserting the blocking pin 2 into said recess 12.

For this purpose, the pin 2 can be fixed in an easily detachable manner to the end of the insertion rod 6, for example by means of an elastic adapter (not shown), of which a detailed description is not necessary for a clear understanding of the principle of its function.

The insertion rod 6 and the conical pin 2 held detachably at the end thereof are introduced into the channel 52 of the implant holder 5. The insertion rod 6 is provided with an external thread below gripping means such as a fluted head 61, as shown. This thread (not shown) cooperates with the internal thread 53 of the implant holder 5. In this way, the insertion and then the screwing of the insertion rod 6 into the channel 52 of the implant holder 5 drives the conical pin 2 into the recess 12 of the wedge 1. The pin 2 can thus be engaged in the conical and unthreaded portion of the recess 12, as has been indicated above, by screwing the insertion rod into the implant holder. After the insertion rod has been screwed fully into the implant holder, the pin 2 is engaged completely in the conical portion of the recess 12. It then comes into engagement with the inner wall of the recess by clamping the flexible link 4 against this wall. The crushing of the braid, which results from this clamping, gives some elasticity, albeit very slight, to the engagement of the pin against the inner wall of the recess.

The implant holder 5 can then be unscrewed from the wedge 1, optionally after unscrewing the insertion rod from the implant holder (not obligatory). The pin 2 then detaches automatically from the end of the insertion rod 6 remaining in place in the unthreaded conical portion of the recess 12. For this purpose, the force with which the pin 2 is elastically connected to the end 62 of the insertion rod 2 is calibrated so as to be less than the clamping pressure applied to the pin 2 by the inner wall of the unthreaded conical portion of the recess 12 when the pin is engaged completely therein.

During the procedure of inserting the pin 2 into the recess 12, the stabilizing wedge 1 can be held by the surgeon in a position with the cords 4a and 4b of the strap 4 engaged around the spinous processes of the vertebrae to stabilized, thanks in particular to the gripping zone of the implant holder 5. The implant holder thus simultaneously serves to maintain the stabilizing wedge in position against the vertebrae in the critical step of inserting the blocking pin of the flexible link 4, but also as a guide for inserting the pin through the rod 6 which slides in the internal channel 52 of the implant holder and screws onto the latter.

Once the implant holder 5 has been separated from the wedge 1 (which is thus already in a situation stabilizing the vertebrae), the locking screw 3 can be engaged in the internally threaded portion 11 of the recess 12 provided in the wedge, as is shown in FIG. 6A and in FIG. 6B. It will be noted that, in this step, the flexible link is already blocked by the pin 2, by clamping of the end portions 41a and 42a against opposite portions of the inner wall of the recess 12, as shown in FIG. 5A and in FIG. 5B.

The screw 3 and the conical pin 2 allow the clamping pressure exerted on the flexible link 4 to be controlled without recourse to a device for measuring the force or the torque.

For this purpose, the length of the conical pin 2 along its longitudinal direction is calibrated such that its plane contact surface 22 is very slightly above the countersink of the internally threaded hole of the stabilizing wedge 1 when it is inserted according to the technique described above. The plane bearing face 32 of the screw 3 then abuts against the countersink of the internally threaded hole 11, hence abutting against the plane contact surface 22 of the conical pin 2, at the rear end, as is shown in FIG. 7A and in FIG. 7B.

The screw 3 is screwed into the internally threaded hole 11 by hand for example, or with the aid of a screwdriver, for example one with a hexagonal head. When the plane surface 32 of the clamping screw comes into contact with the contact surface 22 of the blocking bolt, the clamping screw drives the blocking pin 2 farther into the recess 12, until the plane surface 32 of the clamping screw meets the countersink of the internally threaded hole 11 which forms a shoulder. The axial advance of the conical pin 2 is then blocked by this shoulder, ensuring that the pressure exerted by the conical pin 2 on the flexible link 4 no longer increases, even if the surgeon continues to exert a torque on the clamping screw 3 with the aid of the screwdriver.

In this position, the screw 3 prevents any movement of the pin 2 that would tend to make it leave the recess 12, for example under the effect of tension exerted on the flexible link 4 by the everyday movements of the patient. This is the locking function of the screw 3 in accordance with the principle of the embodiments of the invention. It is understood that this function is radically different from that of the screw described in the documents EP 2192863 and EP 2303163. It is exerted in cooperation with the conical pin 2 which, in functional and structural terms, is radically different from the movable component of the implant described in these documents. The originality of the function of the blocking pin according to embodiments of the invention lies in the direction of movement of the pin, which is orthogonal to the direction of the force with which the pin bears against the surface of the strap 4 and against the inner wall of the recess 12 provided in the wedge.

The stabilizing wedge 1 can be made of a polymer, for example polyether ether ketone (PEEK). It can be obtained by machining from a bar or block of raw material, by injection molding, 3D printing, or by any other equivalent technique.

The conical blocking pin 2 is preferably made of titanium alloy, chosen for its mechanical strength and its biocompatibility. It is provided with a rounded end at the more tapered end in order to facilitate its passage between the tensioned strap portions of the flexible link. It can be obtained, for example, by machining from a bar of raw material.

The clamping and locking screw 3 can also be of titanium alloy, for the same reasons and with the same advantages. It can be obtained by machining from a bar of raw material.

The flexible link 4 is preferably manufactured as a braided textile. As has already been mentioned above, the ends of the flexible link can be stiffened so as to facilitate their gripping and their guiding through the passages 13, 14 and 17 provided in the body of the stabilizing wedge 1.

The present invention differs from the invention described in the document EP 2192863 in particular in the sense that the dynamically stabilizing wedge does not have a part moving perpendicularly with respect to the surface of the strap, i.e. in a lateral direction. On the contrary, the pin moves exclusively along the axis of the posterior approach. The solution described in the present description also makes it possible to install a locking screw 3 which provides safety (locking in position) of the blocking pin 2 of the strap 4, and it permits control of the exerted pressure by virtue of the control of the axial movement of the pin 2 in the recess 12. This screw is also put in place and clamped along the direction of the axis of the posterior approach.

In other words, and following the main advantage of the embodiments described, no action on the part of the surgeon and no movement of a movable component is performed along a lateral direction. Everything is done along the axis of the posterior approach.

The invention has been described and illustrated in the present detailed description and in the figures, in particularly advantageous embodiments. However, it is not limited to the embodiments presented. Other variants and embodiments may be deduced and implemented by a person skilled in the art upon reading the present description and the attached drawings.

In the claims, the terms "comprises" or "has" do not exclude other elements or other steps. The various features disclosed and/or claimed may be advantageously combined. Their presence in the description or in various dependent claims does not exclude this possibility. The reference signs must not be understood as limiting the scope of the invention.

The invention claimed is:

1. An intervertebral implant comprising:
   a stabilizing wedge (1) adapted to stabilize at least two adjacent vertebrae by interposition between spinous processes of said vertebrae, having a substantially parallelepipedal body which has a defined main axis,
   at least one strap (4) forming a flexible link for fixing the stabilizing wedge to the spinous processes of the vertebrae to be stabilized, said strap having first and second strap portions (41a, 42a) which each comprise one of opposite ends (41, 42) of said strap, and said strap having a defined longitudinal direction and a defined strap surface,
   at least one movable assembly (2) adapted to come into engagement with the stabilizing wedge in such a way as to immobilize the strap with respect to the stabilizing wedge by clamping of said strap between said movable assembly and said stabilizing wedge, and
   a locking member (3) for axially locking the engagement of the movable assembly with the stabilizing wedge and thus blocking of the strap, wherein
   the body of the stabilizing wedge comprises at least one recess (12) through which at least the first strap portion can pass, said at least one recess having a longitudinal axis parallel to the main axis of the stabilizing wedge, and an inner wall extending parallel to said longitudinal axis of the recess with a defined shape;
   the movable assembly (2) comprises at least one blocking pin having a defined longitudinal axis and a defined shape substantially complementing a shape of the recess, in order to come into engagement with the stabilizing wedge by movement in said recess in a direction of the main axis of the body of said wedge in such a way that the longitudinal axis of the blocking pin:
      firstly coincides with the longitudinal axis of the recess;
      secondly is perpendicular to a longitudinal axis of the first strap portion inside the recess; and
      thirdly is parallel to a surface of the first strap portion inside the recess,
   and moreover in such a way that the strap portion inside the recess is immobilized with respect to the stabilizing wedge by clamping of said strap portion between the blocking pin and the inner wall of the body of the stabilizing wedge delimiting said recess.

2. The intervertebral implant as claimed in claim 1, in which:
   each of the first and second strap portions can pass through the recess provided in the stabilizing wedge, in order for the strap to form at least one loop in a plane perpendicular to the main axis of the wedge, with a cord adapted to come into engagement with one of the spinous processes of two vertebrae to be stabilized, and in which furthermore
   the blocking pin can come into engagement with the stabilizing wedge in the direction of the main axis of the body of said wedge, between each of the first and second strap portions (41a, 42a) inside the recess, in such a way that the longitudinal axis of the pin:
      firstly coincides with the longitudinal axis of the recess;
      secondly is perpendicular to longitudinal axes of each of the two portions of the strap inside the recess; and
      thirdly is parallel to surfaces of each of first and second strap portions inside the recess,
   and moreover in such a way that each of the first and second strap portions is immobilized with respect to the stabilizing wedge by said strap portion being clamped between the pin and respective portions of the inner wall of the body of the stabilizing wedge delimiting said recess that face each other.

3. The intervertebral implant as claimed in claim 2, in which the first and second strap portions can pass in opposite directions through the recess provided in the stabilizing wedge, so as to intersect in said recess, and in order for the strap to form a loop in a plane perpendicular to the main axis of the wedge, with two cords which are located respectively on either side of the stabilizing wedge in said plane and are adapted to come into engagement each with a respective one of the spinous processes of two adjacent vertebrae to be stabilized.

4. The intervertebral implant as claimed in claim 3, in which the recess provided in the stabilizing wedge has a conical shape, and in which the blocking pin has a conical shape complementing the shape of the recess.

5. The intervertebral implant as claimed in claim 3, in which the body of the stabilizing wedge comprises passages (13, 14) for the strap (4), which extend perpendicularly with respect to the main axis (10) of the body (1) of said wedge, of which at least one passage passes through the recess (12), and through which passages at least the strap can slide when it is not immobilized with respect to the stabilizing wedge.

6. The intervertebral implant as claimed in claim 3, in which the strap (4) is a braid made of non-resorbable textile material for medical use.

7. The intervertebral implant as claimed in claim 2, in which the recess provided in the stabilizing wedge has a conical shape, and in which the blocking pin has a conical shape complementing the shape of the recess.

8. The intervertebral implant as claimed in claim 2, in which the body of the stabilizing wedge comprises passages (13, 14) for the strap (4), which extend perpendicularly with respect to the main axis (10) of the body (1) of said wedge, of which at least one passage passes through the recess (12), and through which passages at least the strap can slide when it is not immobilized with respect to the stabilizing wedge.

9. The intervertebral implant as claimed in claim 2, in which the strap (4) is a braid made of non-resorbable textile material for medical use.

10. The intervertebral implant as claimed in claim 2, in which the recess has an internally threaded inlet zone (11) with a diameter larger than a diameter of the recess to the rear of said inlet zone, and in which the locking member is a screw of a same diameter of the diameter of the inlet zone of the recess, with a thread adapted to cooperate with an internal thread of said inlet zone, and with a bearing zone (32) adapted to bear against a contact zone (22) of the blocking pin (2) in the recess (12) when the screw is screwed into the internally threaded inlet zone of the recess.

11. The intervertebral implant as claimed in claim 1, in which the recess provided in the stabilizing wedge has a conical shape, and in which the blocking pin has a conical shape complementing the shape of the recess.

12. The intervertebral implant as claimed in claim 11, in which the body of the stabilizing wedge comprises passages (13, 14) for the strap (4), which extend perpendicularly with respect to the main axis (10) of the body (1) of said wedge, of which at least one passage passes through the recess (12), and through which passages at least the strap can slide when it is not immobilized with respect to the stabilizing wedge.

13. The intervertebral implant as claimed in claim 11, in which the strap (4) is a braid made of non-resorbable textile material for medical use.

14. The intervertebral implant as claimed in claim 1, in which the body of the stabilizing wedge comprises passages (13, 14) for the strap (4), which extend perpendicularly with respect to the main axis (10) of the body (1) of said wedge, of which at least one passage passes through the recess (12), and through which passages at least the strap can slide when it is not immobilized with respect to the stabilizing wedge.

15. The intervertebral implant as claimed in claim 14, in which the strap (4) is a braid made of non-resorbable textile material for medical use.

16. The intervertebral implant as claimed in claim 1, in which the strap (4) is a braid made of non-resorbable textile material for medical use.

17. The intervertebral implant as claimed in claim 1, in which the recess has an internally threaded inlet zone (11) with a diameter larger than a diameter of the recess to the rear of said inlet zone, and in which the locking member is a screw of a same diameter of the diameter of the inlet zone of the recess, with a thread adapted to cooperate with an internal thread of said inlet zone, and with a bearing zone (32) adapted to bear against a contact zone (22) of the blocking pin (2) in the recess (12) when the screw is screwed into the internally threaded inlet zone of the recess.

18. A surgical kit comprising:
   an intervertebral implant as claimed in claim 17,
   an implant holder (5) with a tubular body having an an internal channel (52) with an internal diameter slightly larger than a largest diameter of the blocking pin (2) of the implant, and adapted to be fixed to the body of the stabilizing wedge in such a way that the channel is in parallax with the axis of the recess (12) in said body, and
   an insertion rod (6) for the blocking pin, adapted to slide in the internal channel for placing the blocking pin in the recess of the body of the stabilizing wedge.

19. The surgical kit as claimed in claim 18, in which the tubular body of the implant holder (5) is provided, at a first end, with a thread (51) for cooperating with the internal thread (11) of the recess (12) provided in the body of the stabilizing wedge (1).

20. The surgical kit as claimed in claim 18, in which the implant holder is provided, at a second end, with an internal thread (53) at an inlet of the channel (52), and in which the insertion rod (6) is provided with a thread (61) in order to cooperate with said internal thread in such a way that insertion and then screwing of the insertion rod (6) into the channel (52) of the implant holder (5) drives the pin (2) inside the recess (12) provided in the body of the wedge (1).

* * * * *